(12) United States Patent
Schmieding

(10) Patent No.: US 7,264,634 B2
(45) Date of Patent: Sep. 4, 2007

(54) METHOD AND INSTRUMENTATION FOR OSTEOCHONDRAL REPAIR USING PREFORMED IMPLANTS

(75) Inventor: Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 430 days.

(21) Appl. No.: 10/665,152

(22) Filed: Sep. 22, 2003

(65) Prior Publication Data

US 2004/0059425 A1 Mar. 25, 2004

Related U.S. Application Data

(60) Provisional application No. 60/412,028, filed on Sep. 20, 2002.

(51) Int. Cl.
*A61F 2/28* (2006.01)
(52) U.S. Cl. ............... 623/14.12; 623/23.58; 623/908
(58) Field of Classification Search ............. 623/14.12, 623/16.11, 18.11, 23.58, 23.59, 908
See application file for complete search history.

(56) References Cited

U.S. PATENT DOCUMENTS

| | | | |
|---|---|---|---|
| 5,314,478 A * | 5/1994 | Oka et al. .......... | 623/14.12 |
| 5,713,374 A * | 2/1998 | Pachence et al. .......... | 128/898 |
| 5,919,196 A | 7/1999 | Bobic et al. | |
| 5,981,826 A | 11/1999 | Ku et al. | |
| 6,231,605 B1 | 5/2001 | Ku | |
| 6,488,033 B1 * | 12/2002 | Cerundolo .......... | 128/898 |
| 2001/0029399 A1 | 10/2001 | Ku | |
| 2001/0039455 A1 * | 11/2001 | Simon et al. .......... | 623/23.51 |

* cited by examiner

*Primary Examiner*—David H. Willse
(74) *Attorney, Agent, or Firm*—Dickstein Shapiro LLP

(57) ABSTRACT

Osteochondral repair of damaged articular joint surfaces is achieved using implants in the form of cylindrical osteochondral plugs. The plugs have an articular surface formed on at least one end. If articular surfaces are provided on both ends of the implant, the articular surfaces have differently curved surfaces. The defective cartilage is removed to create a recipient socket for the implant. An implant sized to fit the recipient socket is chosen from a plurality of implants provided to the surgeon. The implants are preferably formed of a hydrogel material such as Salubria™, although metal or allograft implants can also be used.

8 Claims, 5 Drawing Sheets

METHOD AND INSTRUMENTATION FOR OSTEOCHONDRAL REPAIR USING PREFORMED IMPLANTS

This application claims the benefit of U.S. provisional patent application No. 60/412,028, filed Sep. 20, 2002.

BACKGROUND OF THE INVENTION

1. Field of the Invention

The present invention relates to surgical treatment of isolated articular chondral defects and, more specifically, methods and apparatus for replacement of articular cartilage in knees having chronic anterior cruciate ligament (ACL) deficiency, or isolated articular defects, using reversible synthetic biogel implants for transplantation of articular cartilage in a joint.

2. Description of the Related Art

Chondral defects, i.e., defective cartilage, of the femoral condyles can vary from superficial blemishes and fissures, to large, full-thickness defects. These lesions may be secondary to ligament damage, or may occur as isolated pathology in cruciate normal knees. Treatment has been difficult and controversial. Thus, in many known methods, other indications in the knee are treated, but the chondral lesions usually are left untreated. This approach leads to lesion enlargement and ultimately an advancing arthritic condition.

Chondral defects of the femoral condyles have become widely recognized indications which comprise approximately five percent of all knees undergoing arthroscopy. As such, chondral defects in the knee can be treated by autograft transplantation of bone cores in the knee, as described in U.S. Pat. No. 5,919,196, the disclosure of which is hereby incorporated by reference. However, autografts require additional surgical intervention, increased pain and infusion, and only provide a maximum of 2 or 3 cores to treat smaller focal defects. Furthermore, the donor core must be taken from a location different from the recipient site, thus preventing a perfect match in curvature of the cartilage surface.

As an alternative to the above-described autograft method of treating focal osteochondral defects, an allograft osteochondral transplantation method is known in which a surgeon is provided with a whole cadaver knee from a tissue bank, along with an instrument set containing the full range of sizers and sized instruments. In this allograft method, the surgeon must determine the size of the graft needed and then harvest the properly sized allografts at the time and location of performing the surgery. This method can present certain drawbacks, however, due to several factors, including the preoperative preparation required for the surgeon to harvest and prepare the donor core, the waste from discarding each cadaver knee after the one operation without realizing the full potential for each knee to yield multiple allograft cores, and the comprehensive instrumentation system which must be sent to and recovered from the operation site. A system for harvesting donor cores from a synthetic body part is disclosed in U.S. provisional application No. 60/403,472, filed Aug. 15, 2002, the disclosure of which is incorporated herein by reference.

Moreover, many times the surgeon will determine the presence of a chondral defect during treatment of another condition, and must schedule another surgery to repair the chondral defect. In such instances or in other situations when the surgeon is able to determine the size of the defect prior to the time of the scheduled surgery to repair the chondral defect, the surgery would be much less time-consuming and less burdensome if the surgeon could obtain an appropriately sized, ready-to-use donor graft, prior to the start of the surgery on the patient.

Accordingly, it would be desirable to provide a method of repairing chondral defects using synthetic cores which are formed to the correct size and prepared for transplantation using corresponding instruments.

Various types of synthetic materials for replacement of chondral tissue are known. Salubria™, an elastic biomaterial, sold by Salumedica of Atlanta, Ga. is a hydrogel composition which is similar to human tissue in its mechanical and physical properties. See U.S. Pat. Nos. 5,981,826; 6,231,605, and published application Ser. No. 2001/0029399, the disclosures of which are incorporated herein by reference.

The Salubria™ organic polymer-based material is highly biocompatible and hydrophilic. The hydrogel contains water in proportions similar to those of human hyaline cartilage tissue. Salubria™ closely matches the compliance of human tissue, and has proven to be exceptionally wear resistant and strong, able to withstand millions of loading cycles, making it highly useful as a synthetic osteochondral implant material. Salubria™ can be molded into anatomic shapes and sterilized, making it highly suitable for orthopedic applications.

SUMMARY OF THE INVENTION

The present invention is directed to methods and systems of osteochondral repair using preformed chondral implants. The method includes the steps of creating a recipient socket, selecting one of a plurality of preformed implants to fit the socket, and inserting the selected implant into the recipient socket.

A set of osteochondral implants are delivered to the surgeon to provide a choice of various sizes and curvatures to match the extent and position of the chondral defect. The cylindrical implants have different curvatures and/or contours on each end, providing at least two options for matching chondral surfaces.

The present invention is also directed to an instrumentation set for performing osteochondral repairs with synthetic implants. The instrumentation set includes a recipient harvester, a cannulated counterbore, and a delivery tube.

Other features and advantages of the present invention will become apparent from the following description of the invention which refers to the accompanying drawings.

DETAILED DESCRIPTION OF THE PREFERRED EMBODIMENT

Figure 1:
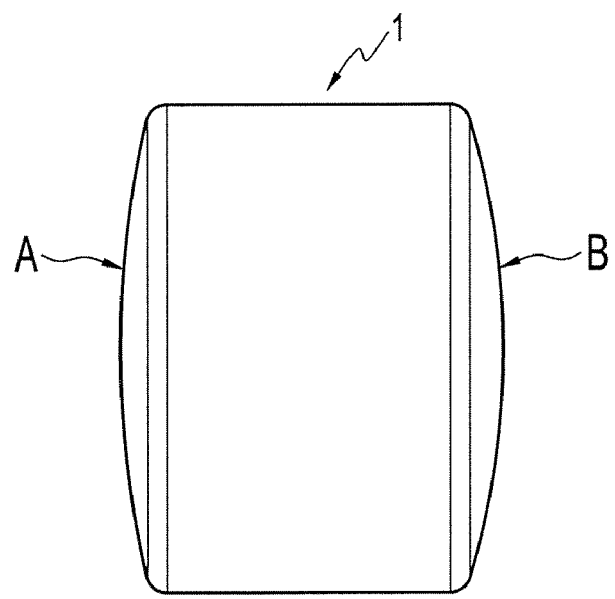
FIG. 1 illustrates a side elevation of a cylindrical synthetic implant having differing curvatures on each end according to the present invention.
Figure 2:
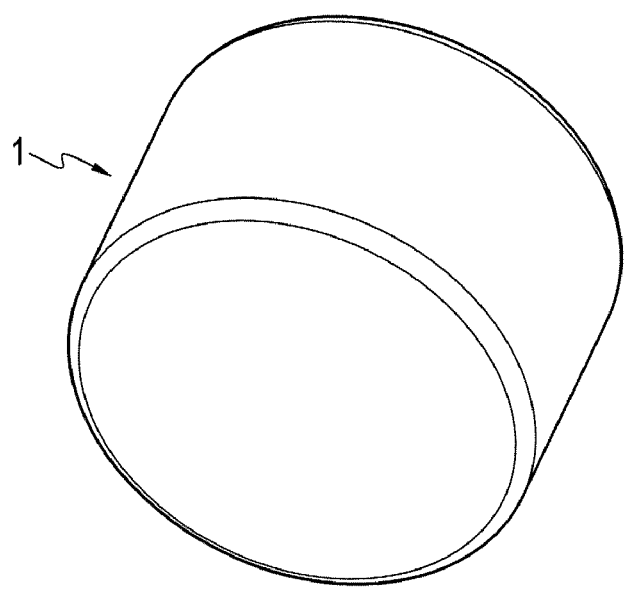
FIG. 2 illustrates a perspective view of the cylindrical implant of FIG. 1.

Referring initially to FIGS. 1 and 2, a cylindrical implant 1 according to the present invention is shown. Preferably, a series of implants 1 are created from a synthetic hydrogel (preferably Salubria™) and delivered to the surgeon with instrumentation for osteochondral transplantation. Each implant is cylindrical, with each end being contoured to match a portion of an articular surface.

The implants are manufactured by forming a cylindrical plug from a synthetic material. Alternatively, the implants can be formed of metal or allograft bone. An articular surface is established on at least one end of the cylindrical plug. If the implant has articular surfaces on both ends, each one preferably has a different contour.

More specifically, FIGS. 1 and 2 show a preformed cylindrical implant 1 provided with curved surfaces on both ends, the curvatures being different, so that each implant provides at least two options for matching the condylar surface being repaired. For example, implant 1 has a simple curved surface on both ends, with one end having a radius of curvature equal to A, and the other having a radius of curvature equal to B. In the example shown, radius A is larger than radius B. Implants preferably are provided in 10 mm and 15 mm diameter sizes. For the example shown in FIGS. 1 and 2, implant 1 has a 15 mm diameter, radius A is 31.75 mm, and radius B is 25.40 mm.

Although the surface of implant 1 has a surface with a simple radiused curvature, other implants are contemplated by the invention in which the contour of each surface is more complex, being for example partially elliptical, or having any other regular or irregular shape. In the series provided to the surgeon, the available curvatures or contours also vary between implants, to provide the surgeon with a range of options for matching the articular surface being repaired. The surgeon uses the provided instrumentation to select and install an appropriately sized implant for osteochondral repair. The procedure is described below, with reference to the accompanying drawings.

Figure 3:
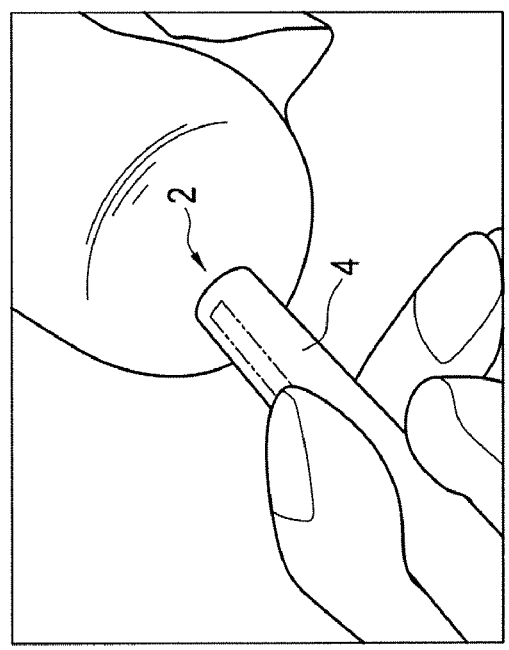
FIG. 3 illustrates a step of sizing an area surrounding a defective articular chondral surface to be repaired according to the present invention.

Referring to FIG. 3, following standard pre-operative examination and diagnostic studies confirming the size and extent of a lesion, a standard para-patellar arthrotomy is carried out to expose the defective articular surface 2. A clear sizer 4 is selected to estimate and approximate coverage of the lesion. Sizer 4 is centered over the defect completely flush (perpendicular) to articular surface 2 in all planes. A 2.4 mm guide pin 6 (shown in place in FIG. 6) is drilled into the defect, preferably at least 20 mm deep.

Figure 4:
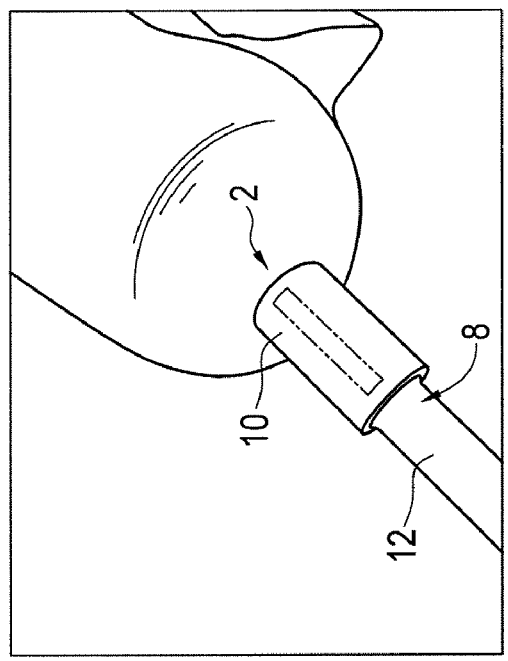
FIG. 4 illustrates a step of scoring the articular surface in a further step of osteochondral repair according to the present invention.

Referring to FIG. 4, the sizer is removed, leaving the guide pin 6 in place, and a recipient harvester 8 placed over the guide pin is used to score the articular cartilage, down to subchondral bone. Recipient harvester 8, provided as a cannulated cutting tube 10 having a handle 12 at one end, is described further in U.S. Pat. No. 5,919,196, the disclosure of which is incorporated herein by reference.

Figure 6:
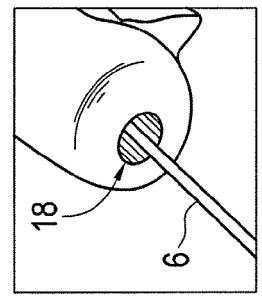
FIG. 6 shows the formed recipient socket with a guide pin left in place according to the present invention.
Figure 5:
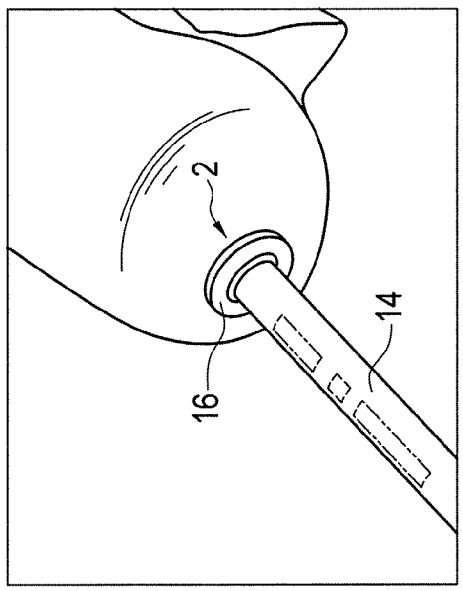
FIG. 5 illustrates a step of forming a recipient socket using a cannulated counterbore according to the present invention.

Referring to FIG. 5, the recipient harvester 8 is removed after scoring the articular cartilage, and a cannulated counterbore 14 is placed over guide pin 6. Counterbore 14 is drilled into the defect until a 10 mm depth stop collar 16 contacts the articular surface 2. The counterbore is removed with the drilled core, as shown in FIG. 6, leaving a recipient socket 18.

Figure 7:
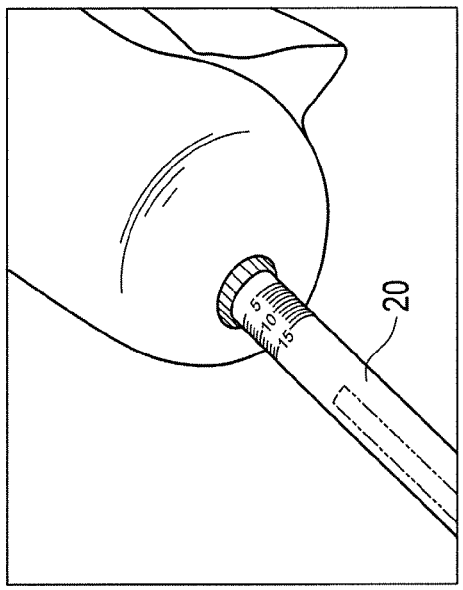
FIG. 7 illustrates a step of dilating the recipient socket according to the present invention.

Referring to FIG. 7, a cannulated dilator 20 is placed over guide pin 6 and inserted to a depth of 10 mm using a mallet. Insertion of cannulated dilator 20 provides minimum dilation, and produces a smooth tunnel wall and socket base for implant insertion.

Figure 8:
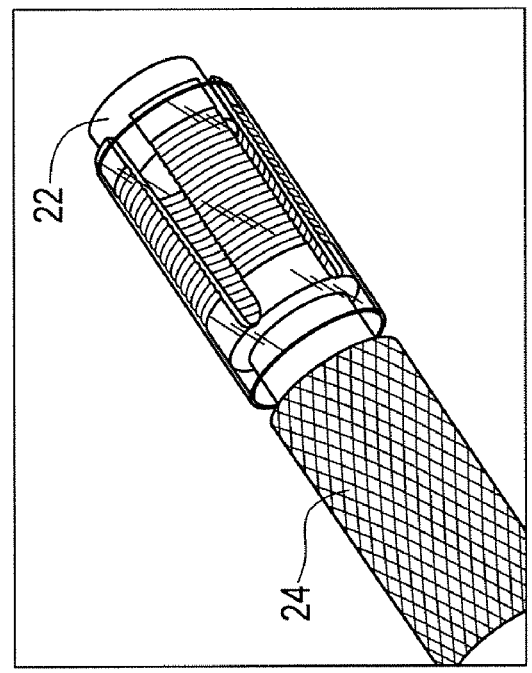
FIG. 8 illustrates a step of loading an implant into a delivery tube according to the present invention.

Referring to FIG. 8, a hydrogel implant 22 is loaded into a delivery tube 24, with the selected articular surface entering the delivery tube first. Sizer 4 is inserted into the opposite end of the delivery tube to prepare for implant insertion.

Figure 9:
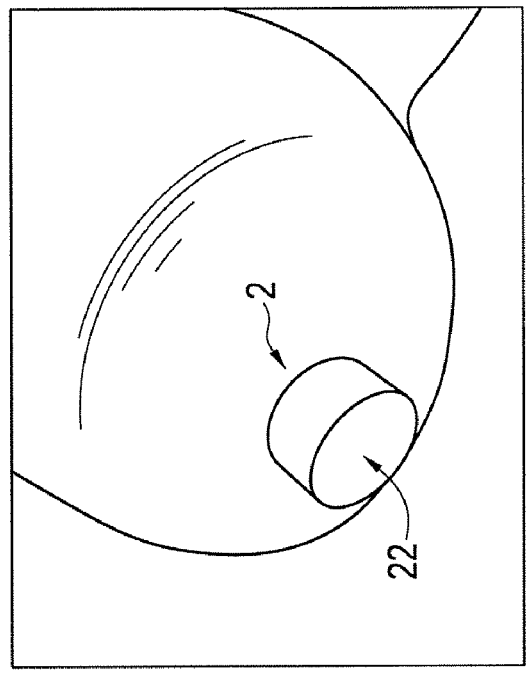
FIG. 9 illustrates a step of inserting the implant into the recipient socket according to the present invention.
Figure 11:
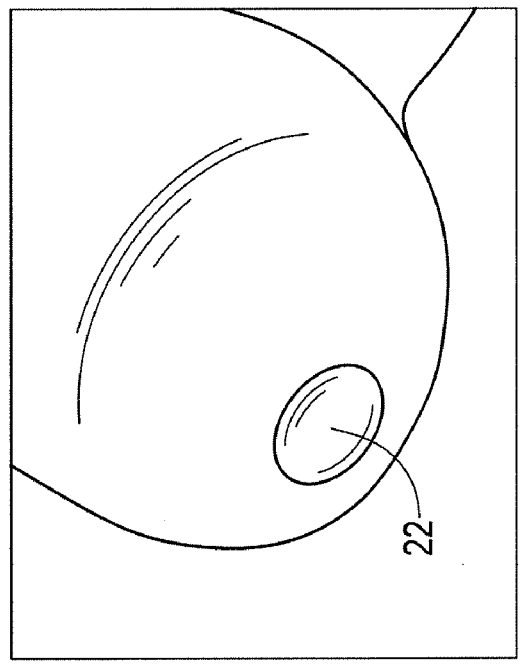
FIG. 11 illustrates the resulting implant fitting flush to the surrounding articular cartilage according to the present invention.
Figure 10:
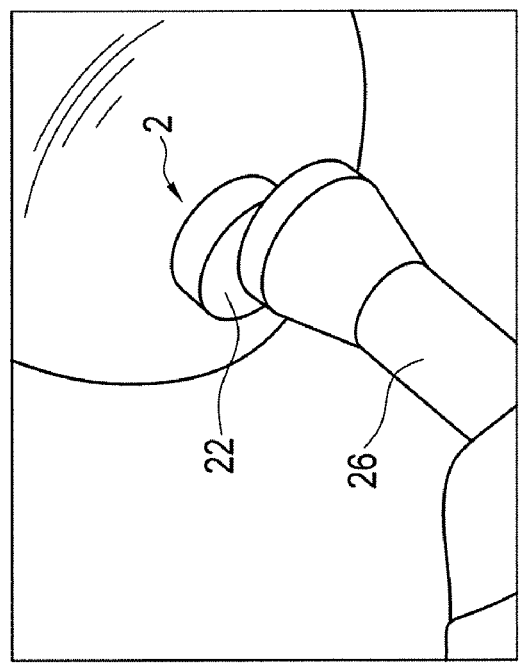
FIG. 10 illustrates a step of seating the implant in the recipient socket using a tamp according to the present invention.

Referring to FIG. 9, implant 22 is partially inserted through the delivery tube into the recipient socket. As shown in FIG. 10, a tamp 26 is used for final implant seating. FIG. 11 shows the implant 22 fitting flush to the surrounding articular cartilage. Optionally, although not shown, the implant can be inserted with a surrounding suture net, or the implant can be provided with a perforated or irregular surface, to prevent movement of the implant in the socket.

Although the present invention has been described in connection with respect to certain preferred embodiments, many modifications and variations will become apparent to those skilled in the art.

What is claimed as new and desired to be protected by Letters Patent of the United States is:

1. A method of osteochondral repair, comprising the steps of:
   creating a recipient socket in bone having a condylar surface to be repaired;
   selecting an implant from a set of implants to match the condylar surface to be repaired, the set comprising a plurality of preformed implants having different curvatures and contours, each of the implants of the set comprising a cylindrical plug having a first end and a second opposing end, the first and second opposing ends being provided with a first surface and a second opposing surface, respectively, the first surface having a first curvature with a first radius and the second opposing surface having a second curvature with a second radius, the first radius being different from the second radius, so that each end is provided with a surface having a different curvature from the surface at the opposing end of the implant;
   matching one of the first and second curvatures of the cylindrical plug with the condylar surface to be repaired; and
   inserting the implant into the recipient socket.

2. The method of claim 1, wherein the implant is formed of hydrogel.

3. The method of claim 2, wherein the hydrogel implant is secured into the recipient socket by disposing a suture net around the implant.

4. The method of claim 2, wherein the hydrogel implant is provided with a perforated surface to secure the implant in the recipient socket.

5. The method of claim 1, wherein the implant is formed of metal.

6. The method of claim 1, wherein the step of inserting the implant comprises loading the implant into a delivery tube and delivering the implant by hand into the recipient socket.

7. The method of claim 1, wherein the opposing surfaces of the implants have a different contour from each other.

8. The method of claim 1, wherein the set of preformed of implants comprises at least two synthetic hydrogel implants, each implant having a different diameter.

* * * * *